United States Patent [19]
Dovichi et al.

[11] Patent Number: 5,741,412
[45] Date of Patent: Apr. 21, 1998

[54] MULTIPLE CAPILLARY BIOCHEMICAL ANALYZER

[75] Inventors: Norman J. Dovichi; Jian Zhong Zhang, both of Edmonton, Canada

[73] Assignee: University of Alberta, Canada

[21] Appl. No.: 735,540

[22] Filed: Oct. 23, 1996

Related U.S. Application Data

[63] Continuation of Ser. No. 413,108, Mar. 29, 1995, Pat. No. 5,584,982, which is a continuation of Ser. No. 072,096, Jun. 3, 1993, Pat. No. 5,439,578.

[51] Int. Cl.$^6$ .................... G01N 27/26; G01N 27/447
[52] U.S. Cl. ............................. 204/602; 204/453
[58] Field of Search .................... 204/451, 452, 204/453, 454, 455, 601, 602, 603, 604, 605

[56] References Cited

U.S. PATENT DOCUMENTS

| | | | |
|---|---|---|---|
| 3,766,047 | 10/1973 | Elevitch | 204/469 |
| 4,284,491 | 8/1981 | Vesterberg | 204/606 |
| 4,305,799 | 12/1981 | Schwartz et al. | 204/455 |
| 4,374,723 | 2/1983 | Vesterberg | 204/617 X |
| 4,574,040 | 3/1986 | Delony et al. | 204/606 |
| 4,675,095 | 6/1987 | Kambara et al. | 204/612 |
| 4,675,300 | 6/1987 | Zare et al. | 204/452 |
| 4,832,815 | 5/1989 | Kambara et al. | 204/612 |
| 4,879,012 | 11/1989 | Kambara et al. | 204/461 X |
| 4,979,824 | 12/1990 | Mathies et al. | 356/318 |
| 5,032,247 | 7/1991 | Tarnopolsky | 204/644 |
| 5,051,162 | 9/1991 | Kambara et al. | 204/612 |
| 5,062,942 | 11/1991 | Kambara et al. | 204/612 |
| 5,091,652 | 2/1992 | Mathies et al. | 204/612 X |
| 5,094,817 | 3/1992 | Aoki et al. | 422/68.1 |
| 5,104,512 | 4/1992 | Gombocz | 204/607 |
| 5,114,551 | 5/1992 | Hjerten et al. | 204/452 |
| 5,192,412 | 3/1993 | Kambara et al. | 204/612 |
| 5,242,796 | 9/1993 | Prober et al. | 204/461 X |
| 5,268,080 | 12/1993 | Kambara et al. | 204/461 |

(List continued on next page.)

FOREIGN PATENT DOCUMENTS

| | | |
|---|---|---|
| 0 294 524 | 12/1988 | European Pat. Off. . |
| 0 723 149 | 7/1996 | European Pat. Off. . |
| 41 39 211 A1 | 11/1991 | Germany . |
| 42 30 354 A1 | 3/1993 | Germany . |
| 43 12 267 A1 | 10/1993 | Germany . |
| 43 13 367 | 10/1993 | Germany . |

OTHER PUBLICATIONS

Hideki Kambara and Takahashi, "Multiple-sheathflow capillary array DNA analyser" Nature, vol. 361 (11 Feb. 1993) 565–566.

(List continued on next page.)

*Primary Examiner*—Kathryn L. Gorgas
*Assistant Examiner*—John S. Starsiak, Jr.

[57] ABSTRACT

A multiple capillary analyzer allows detection of light from multiple capillaries with a reduced number of interfaces through which light must pass in detecting light emitted from a sample being analyzed, using a modified sheath flow cuvette. A linear or rectangular array of capillaries is introduced into a rectangular flow chamber. Sheath fluid draws individual sample streams through the cuvette. The capillaries are closely and evenly spaced and held by a transparent retainer in a fixed position in relation to an optical detection system. Collimated sample excitation radiation is applied simultaneously across the ends of the capillaries in the retainer. Light emitted from the excited sample is detected by the optical detection system. The retainer is provided by a transparent chamber having inward slanting end walls. The capillaries are wedged into the chamber. One sideways dimension of the chamber is equal to the diameter of the capillaries and one end to end dimension varies from, at the top of the chamber, slightly greater than the sum of the diameters of the capillaries to, at the bottom of the chamber, slightly smaller than the sum of the diameters of the capillaries. The optical system utilizes optic fibres to deliver light to individual photodetectors, one for each capillary tube. A filter or wavelength division demultiplexer may be used for isolating fluorescence at particular bands.

24 Claims, 10 Drawing Sheets

U.S. PATENT DOCUMENTS

| | | | |
|---|---|---|---|
| 5,277,780 | 1/1994 | Kambara et al. | 204/603 |
| 5,314,602 | 5/1994 | Kambara et al. | 204/612 X |
| 5,413,686 | 5/1995 | Klein et al. | 204/603 |
| 5,414,508 | 5/1995 | Takahashi et al. | 204/603 |
| 5,439,578 | 8/1995 | Dovichi et al. | 204/603 |
| 5,516,409 | 5/1996 | Kambara | 204/603 |
| 5,529,679 | 6/1996 | Takahashi et al. | 204/603 |
| 5,584,982 | 12/1996 | Dovichi et al. | 204/603 |

OTHER PUBLICATIONS

Hideki Kambara et al., "Multiple Seath–Flor Gel Capillary–Array Electro–phoresis for Multicolor Fluorescent DNA Detection" Analytical Chemistry (1 Apr. 1994) 1021–1026.

Kambara et al., "Photodestruction of fluorophores and optimum conditions for trace DNA detection by automated DNA sequencer" Electrophoresis, vol. 13 (1992) 542–546.

Yung–Fong Cheng and Norman J. Dovichi, "Subattomole Amino Acid Analysis by Capillary Zone Electrophoresis and Laser–Induced Fluorescence" Science, vol. 242 (18 Oct. 1988) 562–564.

Swerdlow et al., "Three DNA Sequencing Methods Using Capillary Gel Electrophoresis and Laser–Induced Fluorescence" Analytical Chemistry, vol. 63 No. 24 (15 Dec 1991) 2835–2841.

Swerdlow et al., "Capillary gel electrophoresis for DNA sequencing. Laser–induced Fluorescence detection with the sheath flow cuvete" Journal of Chromatography, vol. 516 (1990) 61–67.

Kambara et al., "Optimization of Parameters in a DNA Sequenator using Fluorescence Detection" Bio/Technology, vol. 6 (Jul. 1988) 816–821.

Chang et al., "Interaction of Capillary Zone Electrophoresis with a Sheath Flow Cuvette Detector" Analytical Chemistry, vol. 62, No. 5 (Mar. 1990) 496–503.

Huang et al., "Capillary Array Electrophoresis Using Laser–Excited Confocal Fluorescence Detection" Analytical Chemistry, vol. 64, No. 8 (Apr. 1992) 967–972.

Rocheleau et al., "Formamide modified polyacrylamide gels for DNA sequencing by capillary gel electrophoresis" Electrophoresis, vol. 13 (1992) 484–486.

Rocheleau et al., "Separation of DNA Sequencing Fragments at 53 Bases/Minute by Capillary Gel Electrophoresis" Journal of Microcolumn Separations vol. 4, No. 5 (1992) 449–453.

Chen et al., "Two–Label peak–height encoded DNA sequencing by capillary gel electrophoresis: three examples" Nucleic Acids Research, vol. 20, No. 18 (1992) 4873–4880.

Drossman et al., "High–Speed Separations of DNA Sequencing Reaction by Capillary Electrophoresis" Analytical Chemistry, vol. 62, No. 9 (1 May 1990) 900–902.

Swerdlow et al., "Capillary gel electrophoresis for DNA sequencing Laser–induced fluorescence detection with the sheath flow cuvette" Journal of Chromatography, vol. 516 (1990) 61–67.

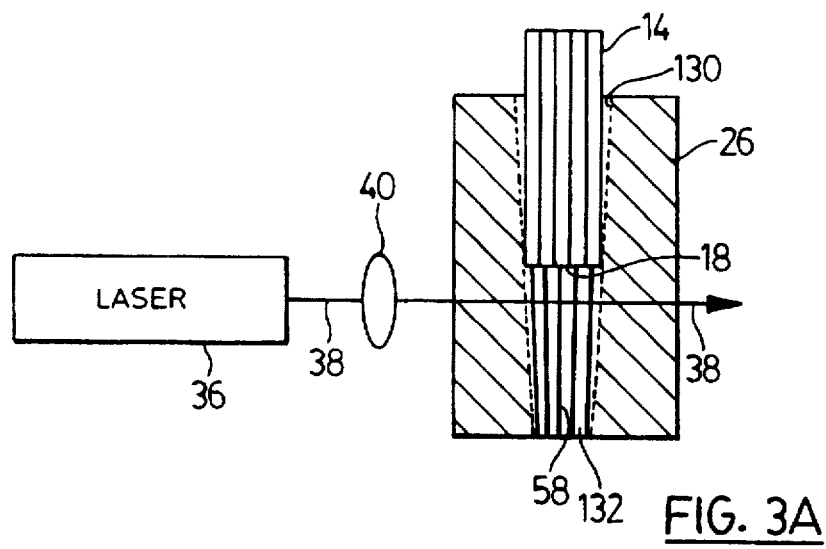
FIG. 3A
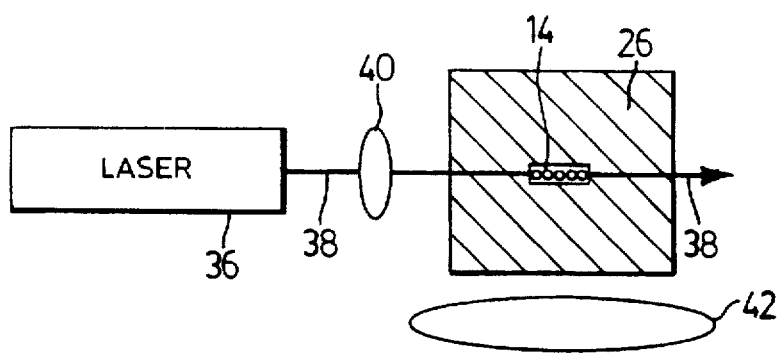
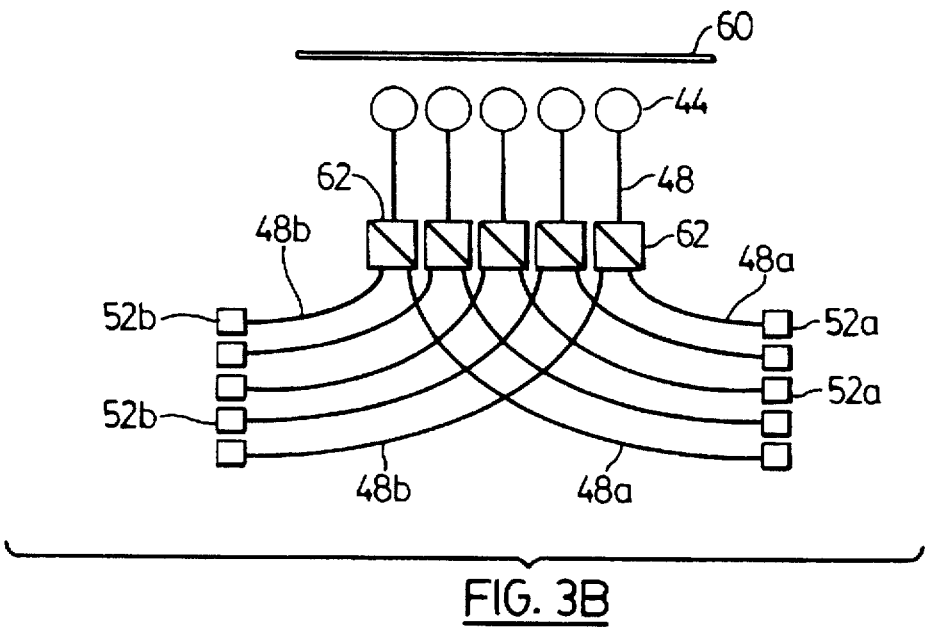
FIG. 3B

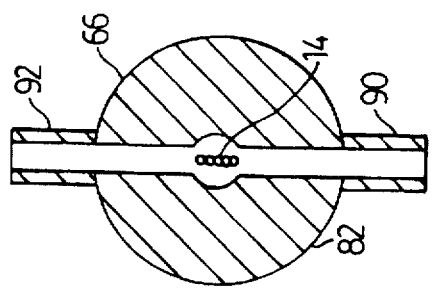
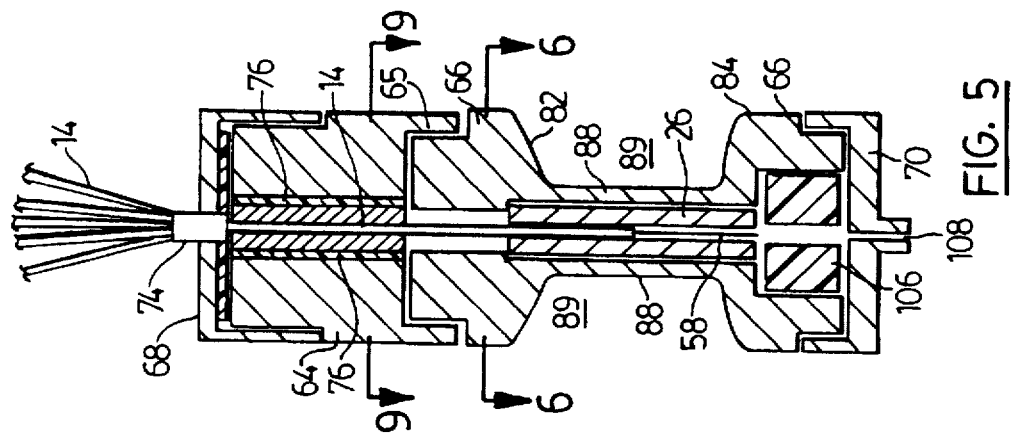
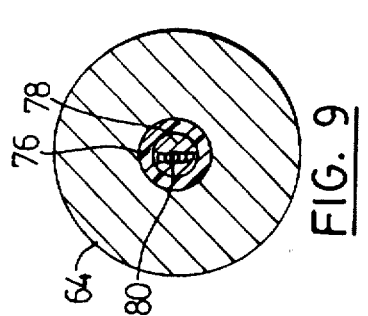
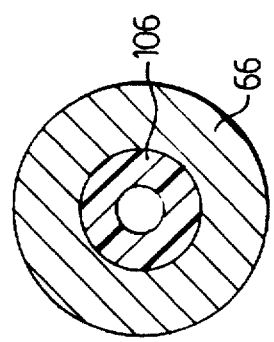
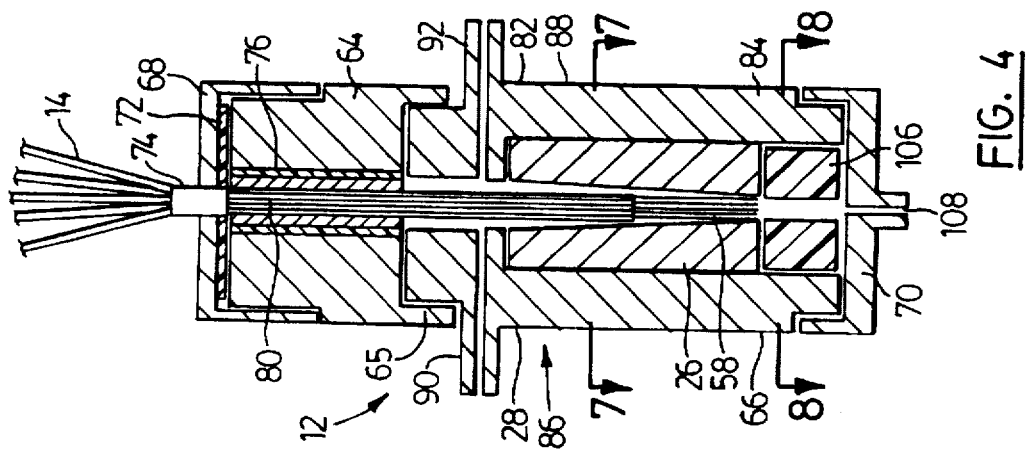

MULTIPLE CAPILLARY BIOCHEMICAL ANALYZER

This is a continuation of application Ser. No. 08/413,108, filed Mar. 29, 1995, now U.S. Pat. No. 5,584,982 which is a continuation application Ser. No. 08/072,096, filed Jun. 3, 1993, now U.S. Pat. No. 5,439,578.

FIELD OF THE INVENTION

This invention relates to apparatus used for biochemical analysis.

BACKGROUND AND SUMMARY OF THE INVENTION

Simultaneous analysis of a large number of biological samples is useful in flow cytometry, DNA sequencing, liquid chromatography, oligonucleotide analysis, zone electrophoresis of proteins, as well as other electrophoretic techniques. In particular, rapid DNA analysis is of importance in the Human Genome Project, which is an attempt to identify the sequence of bases (dideoxynucleotides) in human DNA.

One technique that has been applied to the sequencing of DNA is capillary electrophoresis. In capillary electrophoresis, an appropriate solution is polymerized or gelled to form a porous matrix in a fused silica capillary tube of internal dimensions in the order of 50 μm. An electric filed is applied across the matrix. Fragments of sample DNA injected into one end of the capillary tube migrate through the matrix under the effect of the electric field at speeds that depend on the length of the fragment. Hence, different length fragments arrive at a detection part of the capillary at different times. The dideoxynucleotide at one end of the fragment may be labelled with a fluorescent marker during a reaction step. The fluorescent marker is associated with the terminating dideoxynucleotide. When the fragment passes through a beam of light from a laser in the detection zone, the fluorescent marker fluoresces and the fluorescence may be detected as an electric signal. The intensity of the electric signal depends on the amount of fluorescent marker present in the matrix in the detection zone. The dideoxynucleotide at the end of the fragment may then be identified by a variety of methods. As different length fragments migrate through the matrix under the applied field, a profile of the fragments may be obtained.

The use of three different DNA sequencing techniques is set out in Swerdlow, H. et al, *Three DNA Sequencing Methods Using Capillary Gel Electrophoresis and Laser Induced Fluorescence*, Anal. Chem., 33, 2835–2841, Dec. 15, 1991, and the references cited therein. In the Tabor and Richardson technique (one spectral channel sequencing), a single fluorescent marker is used, and the amount of dideoxynucleotide in the reaction mixture is varied so that each base of the DNA fragment may be identified with a particular fluorescent peak height. For example, the concentration of dideoxynucleotides might be varied in the ratio of 8:4:2:1. The variation in fluorescence intensity with time will then identify the sequence of bases. In the DuPont system (two spectral channel sequencing), succinylfluorescein dyes are used to label four dideoxynucleotides. A single wavelength (488 nm) is used to excite fluorescence from the dyes. Emission is distributed between two spectral channels centered at 510 and 540 nm. The ratio of the fluorescent intensity in the two spectral channels is used to identify the terminating dideoxynucleotide. In the Applied Biosystems system (four spectral channel sequencing), four dyes (FAM, JOE, TAMRA and ROX) are used to label primers to be used with each dideoxynucleotide reaction. Two lines from an argon laser (514.5 and 488 nm) are used to excite fluorescence. Interference filters are used to isolate emission at 540, 560, 580 and 610 nm and peaks of the resulting four electrical signal profiles are used to identify the bases.

Application of capillary electrophoresis to DNA analysis is complicated by the scattering of light from the porous matrix and the capillary walls. For this reason, there has been proposed use of a sheath flow cuvette in which a sample stream of DNA is injected under laminar flow conditions in the center of a surrounding sheath stream, generally of the same refractive index. Such a cuvette is described in Swerdlow H., et al, *Capillary Gel Electrophoresis for DNA Sequencing: Laser Induced fluorescence detection with the sheath flow cuvette*, Journal of Chromatography, 516, 1990, 61–67.

However, the above described methods of DNA sequencing using capillary electrophoresis have used single capillaries and rapid DNA sequencing and other biological process requiring simultaneous analysis of sample streams require use of multiple capillary systems.

One such multiple capillary system is described in Huang et al, *Capillary Array Electrophoresis Using Laser Excited Confocal Fluorescence Detection*, Anal. Chem. 64, 967–972, Apr. 15, 1992. In the Huang device, multiple capillaries lying side by side in a flat array holder are sequentially scanned by a laser beam and fluorescence detected from the capillaries using a photomultiplier tube. Such a device suffers from the same difficulties as with a single capillary that is scanned with a laser, namely that there is light scatter from the capillary walls and interfaces between the matrix and capillary.

The inventors have therefore proposed a multiple capillary analyzer that allows detection of light from multiple capillaries with a reduced number of interfaces through which light must pass in detecting light emitted from a sample being analyzed.

In one aspect of the invention, there is provided a multiple capillary analyzer using a modified sheath flow cuvette. A linear array of capillaries is introduced into a rectangular flow chamber. Sheath fluid draws individual sample streams through the cuvette. The capillaries are closely and evenly spaced and held by a transparent retainer in a fixed position in relation to an optical detection system. Collimated sample excitation radiation is applied simultaneously across the ends of the capillaries in the retainer. Light emitted from the excited sample is detected by the optical detection system.

In a further aspect of the invention, the retainer is provided by a transparent chamber having inward slanting end walls. The capillaries are wedged into the chamber. One sideways dimension of the chamber is equal to the diameter of the capillaries and one end to end dimension varies from, at the top of the chamber, slightly greater than the sum of the diameters of the capillaries to, at the bottom of the chamber, slightly smaller than the sum of the diameters of the capillaries.

In a still further aspect of the invention, the optical system utilizes optic fibres to deliver light to individual photodetectors, one for each capillary tube. A filter or wavelength division demultiplexer may be used for isolating fluorescence at particular bands.

In a still further aspect of the invention, the array may be rectangular, including square, or the like formed of plural rows of capillaries terminating at different levels in a rectangular sheath flow cuvette. A rectangular array of lenses receives light emitted, scattered or reflected from samples emerging from the capillaries and the light is then converted to electrical signals and processed.

BRIEF DESCRIPTION OF THE DRAWINGS

There will now be described a preferred embodiment of the invention, with reference to the drawings, by way of illustration, in which like numerals denote like elements and in which:

FIG. 3A is a section through the chamber of FIG. 1 showing the passage of a laser beam through the chamber;

FIG. 3B is a schematic showing a light collection and detection system for used with the analyzer of FIG. 2;

FIG. 4 is a section through the multicapillary sheath flow cuvette of FIG. 2 (the section is through the center but also shows pedestals, which are off center, and appear behind the chamber);

FIG. 5 is a section at right angles to the section of FIG. 4 (the section is through the center but also shows pedestals, which are off center, and appear behind the chamber);

FIG. 6 is a section along the line 6—6 in FIG. 5 showing the inlet for sheath fluid;

FIG. 7 is a section along the line 7—7 in FIG. 5 showing the off center pedestals that retain the flow chamber;

FIG. 8 is a section along the line 8—8 in FIG. 4 showing the base of the cuvette;

FIG. 9 is a section along the line 9—9 in FIG. 4 showing a split rod with a slot along its central axis for retaining the capillary tubes;

DETAILED DESCRIPTION OF PREFERRED EMBODIMENTS

Figure 1:
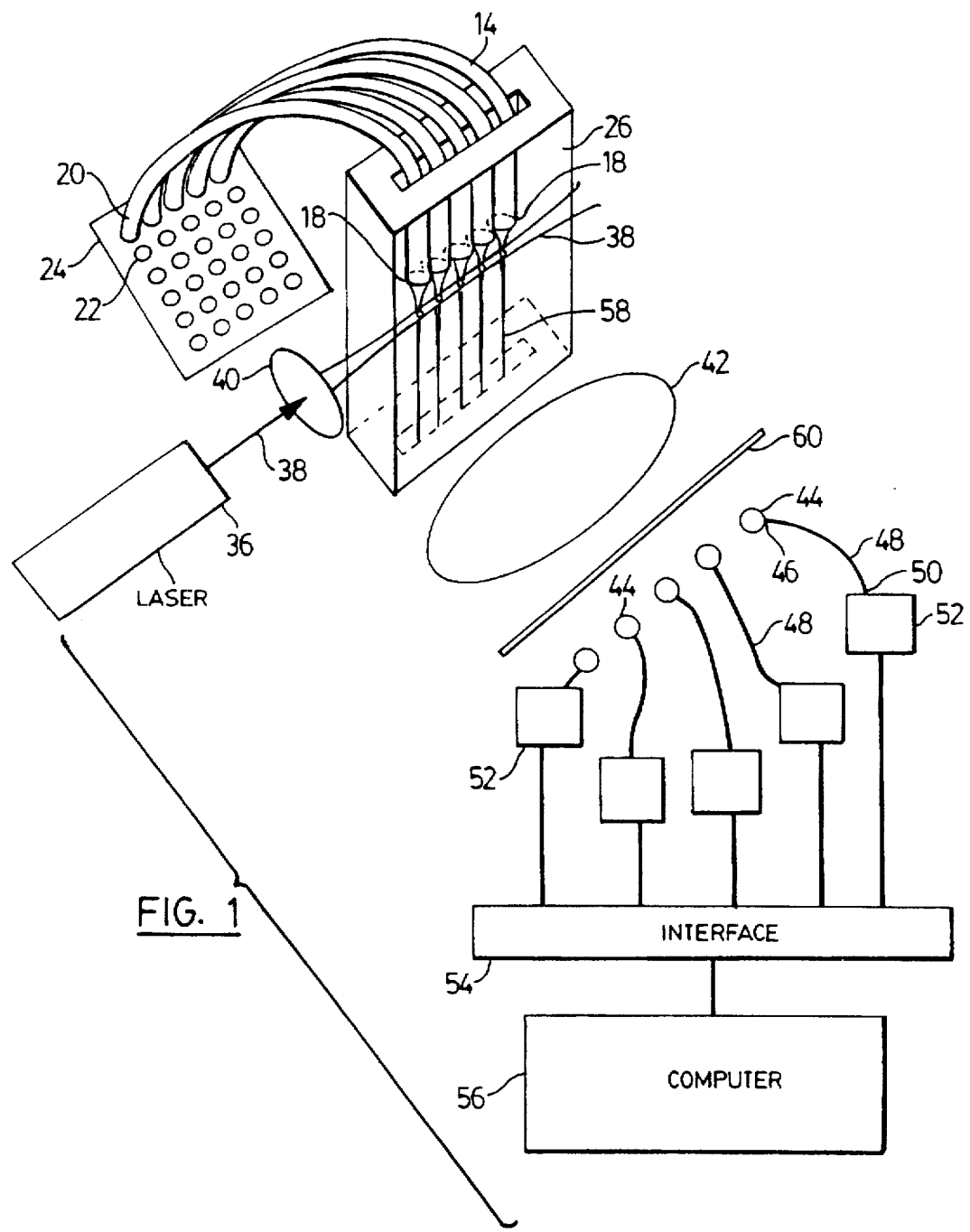
FIG. 1 is an isometric schematic view of an exemplary biochemical analyzer according to the invention showing a sheath flow cuvette, multiple capillaries, a flow chamber and optical system.
Figure 2:
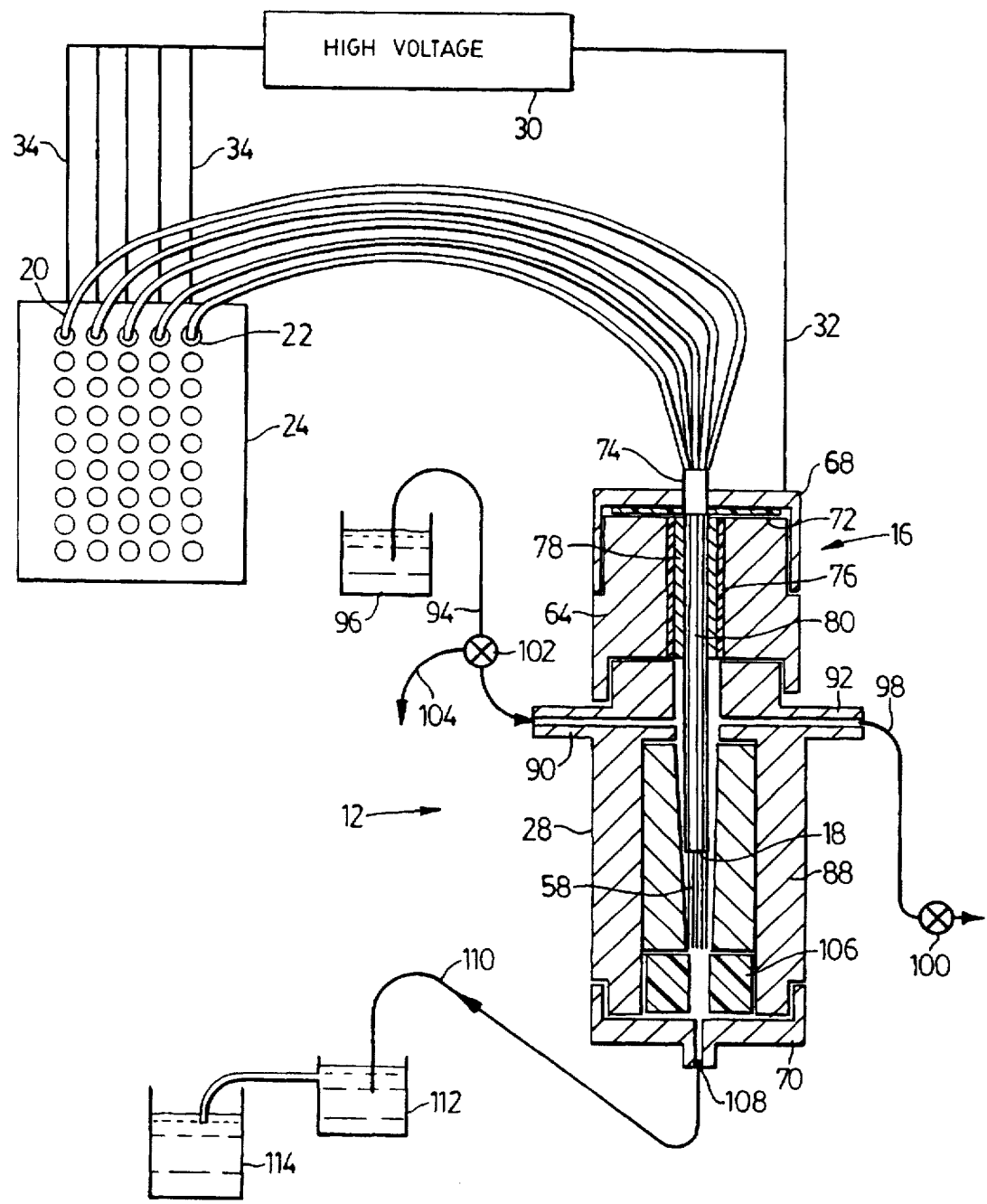
FIG. 2 is a section through the analyzer of FIG. 1 without optical components.

Referring to FIGS. 1 and 2, there is shown an analyzer for analyzing a sample of DNA including a sheath flow cuvette 12 enclosing the ends of five capillary tubes 14 arrayed side by side in a line like the teeth of a comb. The capillary tubes 14 are held in a header 16 with their cleaved ends 18 terminating inside the chamber 12. The other ends 20 of the capillary tubes 14 terminate in five of the wells 22 of a conventional microtiter plate 24. The capillary tubes 14 are conventional fused silica capillaries, with about 50 μm ID and 150 μm OD, available from Polymicro. The cuvette 12 is formed of a quartz chamber 26 secured within a stainless steel holder 28, the design of which is shown in FIGS. 4–9 in more detail. A high voltage source 30, such as a Spellman RHR-30PN60 30 KV power supply, is connected to the stainless steel holder 28 through a first electrode 32 (grounded) and also through five second electrodes 34 to fluid in the wells 22. Thus, when the capillary tubes 14 and chamber 12 are filled with conducting material, a high voltage may be applied across the material in the capillary tubes using the high voltage source 30. The circuit is formed by the grounded electrode 32, the stainless steel holder 28 (formed of cap 68, capillary retainer 64, chamber retainer 66 and cap 70), fluid in the cuvette 12 and in the chamber 26, matrix in the capillary tubes, including sample buffer if present, buffer solution in the wells 22 and the electrodes 34.

A laser 36 or other source of collimated electromagnetic radiation provides a collimated beam 38 of light that is aligned to pass through a focusing lens 40 into the chamber 12 along a projection of the capillary tubes into the chamber, as close as possible to the ends of the capillary tubes 14, as shown in FIG. 3A. The wavelength of the laser 36 is chosen to excite fluorescence in the sample being analyzed, as for example DNA reacted with a fluorophor. An appropriate choice for DNA analysis is an Innova 70-4 argon ion laser available from Coherent Inc. of Palo Alto, Calif. Such a laser may be operated with multiple wavelength mirrors (488 and 514.5 nm), with appropriate selection of the wavelength depending on the method used for sequencing the DNA.

Fluorescence from the sample in the chamber 12 is detected through a collection lens 42 that images the fluorescence on to a plurality of 1 mm aperture GRIN (gradient index) lenses 44 (available from Nipon Scientific Glass through Precision Cells, Inc. of Farmingdale, N.Y.) which are affixed to receiving ends 46 of fiber optics 48. The fibre optics 48 may be secured in known manner as for example to a Melles Griot optical bread board (not shown). Transmitting ends 50 of the fiber optics 48 lead into avalanche photodiodes 52 or other individual photon detectors, one for each capillary tube 14, and whose output is connected through an interface 54 to a computer 56. Exemplary photodiodes 48 are RCA (EG&G) C30902S photodiodes powered by a PS310 Stanford Research System high voltage power supply or model SPCM 100 photodiodes available from EG&G Canada Ltd. Fluorescence is transmitted along the fiber optics 48 to the photodiodes 52 whose electrical output is proportional to the intensity of the fluorescence. Electrical signals output from the photodiodes 52 are passed through a data acquisition board 54 (such as may be obtained from National Instruments or from Data Translation, model DT2221-G) to a computer 56 such as a Macintosh II computer for processing according to known techniques. Such processing includes filtering the signal to give a desired frequency response, and a second filter or phase lock loop to identify the position of the peak centers. For interface boards from National instruments, it may be necessary to decrease illumination intensity to avoid over saturation of the photon detectors. Alternatively, light collected in individual GRIN lenses 44 may be passed through a bundle of optical fibres and imaged onto or abutted against an array detector. However, CCD cameras are not believed to be fast enough for high speed DNA sequencing.

As shown in FIGS. 3A and 3B, if the fluorescence emitted from the DNA sample has a spectrum centered on more than one wavelength of light, then a means of dividing the spectrum of the received light may be used. Light from laser 36 passes through focusing optic 40 and passes through the sample streams 58. Fluorescence from the sample streams is collected by optic 42 and passed through a spectral filter 60 (for filtering scattered light) to GRIN lenses 44 on the ends of fibre optics 48. Light in the fibre optics 48 is passed through wavelength division demultiplexers 62 where light from different spectral bands is separated into two sets 48a and 48b of fibre optics and two sets of avalanche photodiodes 52a and 52b.

The selection of the filter 60 and the optical system depends on the sequencing reaction to be performed. For a single codor sequencer, using the sequencing method of Richardson-Tabor, a single spectral filter 60 with a bandwidth of 45 nm centered at 530 nm may be used to detect fluorescein labeled products. The filter should be selected to minimize background signals due to Raman and Raleigh scatter of the excitation beam 38. For the DuPont sequencing system, two detection channels are required, one detector channel to image light in a band centered at 510 nm and the other to image light centered at 540 nm. Light collected from the collection optic is split into two paths using the wavelength division demultiplexers 62, one path leading to one set of photon detectors 52a and the other leading to the other set of photon detectors 52b. Other methods of wavelength division demultiplexing may be used as for example rapidly switching a filter wheel so that the light from the sample stream is time division demultiplexed. For sequencing using the method developed by Applied Biosystems Inc. (see the Swerdlow article), four channels are required. As with the-DuPont system, two detector systems are used, and a filter wheel may be used as the spectral filter 60 to rotate two selected filters across the path of the light collected by the collection optic. By alternating the two filters in the two detection systems, a signal from four spectral channels may be generated.

The collection optic 42 should be selected to provide an image that is matched in size to the aperture of the GRIN lenses 44, such as may be provided by a flat field high numerical aperture microscope objective, for example as made by Leitz/Wild (0.40 NA achromat objective). With a sample stream diameter of 50 µm and a GRIN lens diameter of 1 mm, for example, the magnification should be about 20×, generating spots several millimeters apart. Since the light from the collection optic tends to expand with a curved wavefront, the GRIN lenses should be arranged to have their collection faces perpendicular to radii of the wavefront.

Referring to FIGS. 4–9, the chamber 26 is held in a stainless steel holder 28 to form a sheath flow cuvette. The holder 28 includes an upper section or capillary retainer 64 and a lower section or chamber retainer 66 each machined from individual pieces of steel rod. The retainers 64 and 66 are threaded together at 65 (threads not shown). A top cap 68 is threaded onto the upper end of retainer 64. A bottom cap 70 is threaded onto the lower end of retainer 66. An upper seal 72 made of plastic forms a seal between the cap 68 and retainer 64. A like seal (not shown) may be used to seal the cap 70 to the retainer 66. An O-ring (not shown) or other suitable seal should be provided to ensure that the retainers 64, 66 are sealed together to prevent leakage at 65. The cap 68 has a central hole for receiving the capillary tubes 14. A plastic sleeve 74 into which the capillaries are threaded has epoxy applied to it to form a seal around the capillary tubes 14 as they enter the cap 68. The capillary retainer 64 includes a hollow bore lined with a plastic cylindrical and annular spacer 76. Filling out the hollow bore of the retainer 64 are two facing semi-circular metal rods 78 each with a groove machined into their facing flat faces to form a rectangular slot 80. The slot 80 is dimensioned to receive the capillaries 14 snugly and hold them against each other in a line.

The chamber retainer 66 includes two circular sections 82 and 84 and a pedestal section 86 in which the metal of the rod has been machined away to form four pedestals 88 in which the chamber 26 is securely retained. Metal in the chamber retainer 66 is machined away in the pedestal section 86 to form cavities 89. Removal of the metal in this section 86 allows a microscope objective to be placed close to the chamber 26 (within a few millimeters). Upper circular section 82 includes a sheath fluid inlet 90 and a bubble removal port 92. The sheath fluid inlet 90 is connected via Teflon™ tubing 94 (see FIG. 2) to a source of sheath fluid 96 (not shown to scale). The bubble removal port 92 is connected by Teflon™ tubing 98 to a valve 100. The tubing 94 may include a three way valve 102 with waste line 104 for removing bubbles from the sheath fluid. In the chamber retainer 66, at the base of the chamber 26 is a plastic bottom plug 106 that holds the chamber 26 in place. The cap 70 is provided with a waste outlet port 108 that is connected to Teflon™ tubing 110 to a waste beaker 112.

As shown in FIG. 2, sheath fluid is provided through inlet 90. The sheath fluid enters the top of the chamber 26 and moves as a syphon flow under gravity from the top of the chamber to the bottom, past the ends 18 of the capillary tubes 14. The fluid should be provided in a steady, non-pulsed flow, and should be filtered and purified to avoid any background signal passing due to particles passing through field of view of the collection optics. The fluid is chosen to have similar index of refraction as the fluid carrying the sample DNA to avoid reflection and refraction at interfaces between fluids of different indexes of refraction. The simplest way to achieve this is to use the same fluid for the sheath fluid as carries the sample DNA, as for example 1×TBE. The volumetric flow of the sheath stream is low, in the order of less than 10 mL/hr, which for the embodiment described is in the order of 4 mm/s, though it may be as much as 10× less for some applications. The fluid is drained to waste after exiting the chamber 12 through port 108. The waste beaker 112 should be kept half-filled with buffer. If the waste stream forms drops, the sample stream profile is distorted when the drop detaches. A periodic noise results from the periodic detachment of the drops. The beaker 112 preferably has a small hole drilled in it with a tube leading to a larger beaker 114. The level of the first beaker 112 remains constant, so that the sheath flow velocity under conditions of syphon flow changes slowly. A constant syphon head may also assist in ensuring constant sheath flow rate. For the apparatus described a 5 cm syphon head has been found adequate. Bubbles should not be present in the sheath flow. These can be eliminated by visual inspection and eliminated using the three way valve 102 (by switching the fluid containing the bubble to waste).

Figure 10A:
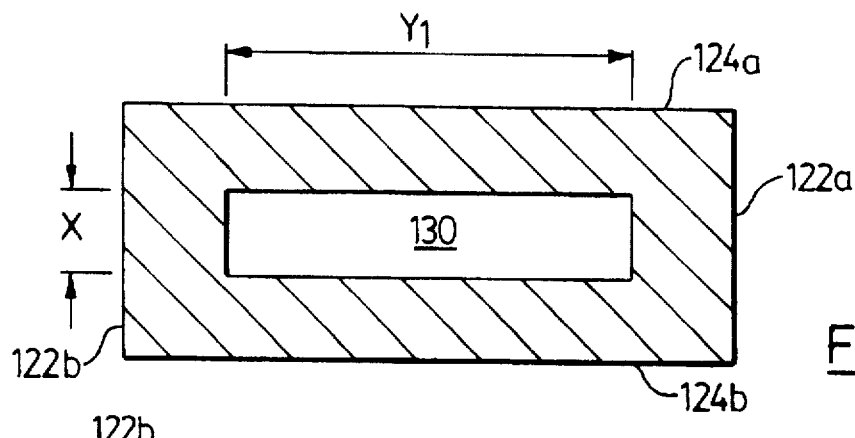
FIG. 10A is section through the top of the sheath flow cuvette.
Figure 10B:
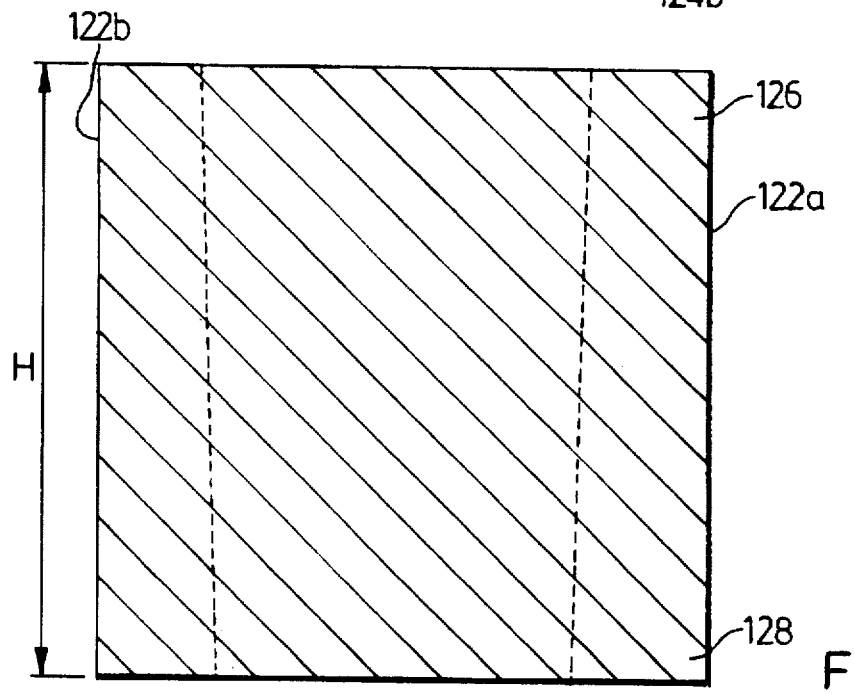
FIG. 10B is longitudinal section through the sheath flow cuvette.
Figure 10C:
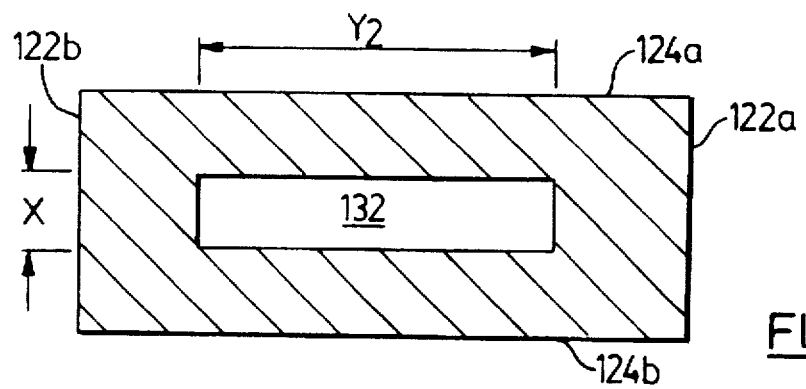
FIG. 10C is a section through the bottom of the sheath flow cuvette.

Referring to FIGS. 10a, 10b and 10c, the chamber 26 includes end walls 122a, 122b, side walls 124a, 124b top 126 and bottom 128. The walls need not be planar but may contain projections to align the capillaries. Each wall is 1 mm thick at the top and made of high quality optical quartz, or such other inert material as is transparent to the selected electromagnetic radiation emitted by either the laser 36 or the sample passing out of the capillary tubes 14. The side walls 124a, 124b are constant thickness from top to bottom, while the end walls each thicken inward towards the bottom by 50 µm. The interior of 130 of the chamber 26 has the same dimension X laterally as the thickness of the capillary tube used (150 µm in the exemplary embodiment) and the dimension $Y_1$ from end wall to end wall a little more (50 µm more in the exemplary embodiment) than the sum of the thicknesses of the capillary tubes 14. The interior 132 at the bottom of the chamber has the same dimension X laterally as the thickness of the capillaries used and the dimension $Y_2$ from end wall to end wall a little less (50 µm in the exemplary embodiment) than the sum of the thicknesses of the capillary tubes 14. The capillary tubes 14 should be snugly fit in the interior of the chamber 26, with their ends terminating adjacent each other. It is preferable that the capillary tubes 14 be placed in the chamber 26 before they are filled with matrix material.

Particularly if capillary tubes are re-used, the collection optics, including the GRIN lenses 44, will be fixed and the capillary tubes 14 must be aligned with the collection optic so that fluorescence from the sample stream irradiated by the laser beam 38 is imaged onto the GRIN lenses 44. The capillary tubes 14 are first inserted through the cap 68 and retainer 64 into the slot 80 formed by the two rods 78. The capillary tubes 14 may be loaded together or one by one. The capillary tubes 14 are inserted into the chamber 26 in this manner and pushed together into the chamber 26 until they are firmly held in the chamber 26. With the chamber 26 of the dimensions stated, the capillary tubes 14 will terminate about half way through the chamber 26. The top of the chamber 26 thus encompasses the capillary tubes 14 with the capillary tubes 14 abutting the interior walls of the chamber at the ends near the center of the chamber and at the sides throughout the length of the capillary tubes within the chamber 26. Abutment of the capillary tubes against the interior walls of the chamber seals any gaps between the capillary tubes at the center of the chamber 26. Unless such gaps are sealed, non-uniformities in the sheath flow can result which can affect the signal quality. The capillary tubes 14 are preferably cleaved at their ends using well known techniques employed in the manufacture of fiber optics in order to obtain a smooth and flat end. The capillary tubes 14 will therefore extend into the interior of the chamber 26 an amount that is dependent on the rate of decrease of the end wall to end wall dimension of the chamber, and will typically be 1 cm for the exemplary embodiment described. The chamber 26 has height H about 2 cm from top to bottom as shown in the example. Such chambers may be purchased from Nipon Scientific Glass through Precision Cells, Inc. of Farmingdale, N.Y., to order. The height H of the chamber is somewhat arbitrary, sufficient to allow both fixture of the capillary tubes and to allow the light beam to pass through the chamber below the capillary ends. 2 cm is chosen to allow addition of a second laser beam below the first if two lasers are used for analysis. The top of the side walls 124a, 124b should be slightly bevelled to ease insertion of the capillary tubes 14. The construction of the chamber is quite important, particularly when the capillary tubes are not electrically isolated from the high voltage applied across the porous matrix material in the capillary tubes. If the capillary tubes are not isolated electrically, repulsive forces between them can create forces which if not evenly distributed, can shatter the capillary tubes. The capillary tubes 14 should therefore all be held securely in the chamber to prevent these stresses from concentrating at one tube.

The capillary tubes 14 should terminate within about 10 µm from each other. The laser beam 38 should entirely pass within about 100 µm from the ends of the capillary tubes. Careful alignment of the capillary tubes is required so that the image of the fluorescence falls directly on the GRIN lenses. This can be checked by passing light backward through the GRIN lenses. The light should pass through the sample stream exactly at the same point that fluorescence due to the laser beam occurs. Visual inspection can be used to verify the correct alignment of the capillary tubes, with appropriate safety precautions due to the use of laser light.

The length of the flow cell (distance between the end walls 124a and 124b) and the number of capillaries that can be detected in a single flow cell are determined by the distance over which laser beam size can be matched to the sample stream radius as it exits the capillary. To optimize sensitivity, the laser beam should be located as near as possible to the ends of the capillaries to minimize effects of diffusion of the sample into the sheath fluid. The laser beam should therefore pass through the acceleration region of the sample flow. At this point, faster moving sheath fluid draws the sample fluid from the matrix. Since the entire cuvette is grounded (through electrode 32), there is very little electric field inside the cuvette, and the sample fluid is not drawn by the electric field out of the capillaries. Thus it is the sheath flow that draws the sample fluid from the matrix in the capillaries. As the sample fluid moves away from the end of the capillary its cross-section contracts, and then expands due to diffusion of the sample fluid into the sheath fluid. The laser beam should pass through a point above the point of maximum contraction, thus before the diffusion zone.

A single laser beam is aligned to be parallel with the long axis of the cuvette (end wall 122a to end wall 122b) simultaneously exciting fluorescence from each sample stream in turn. The size of the laser beam should be selected to ensure similar illumination of each sample stream. With a lens (for example a microscope objective with 1× magnification) between the laser 36 and the chamber 26 a beam waist can be located in the center of the chamber. The beam spot size at the center of the chamber should be equal to the sample stream diameter at that point. With 50 µm ID capillary tubes, this is about 50 µm. The beam diameter will be larger in both directions away from this point, but with this arrangement, the fluorescence is close to optimum.

For setting up the analyzer for DNA analysis, care must be taken as is known for capillary electrophoresis. Thus, the matrix material must be selected for stability, for discrimination of longer base lengths and for speed of sequencing. No one matrix is suitable for all applications. For DNA sequencing, a 0% C (non-cross-linked), 5–6% T acrylamide gel has found to be adequate and has the added advantage of low viscosity which allows it to be readily replaced, without removal of the capillary tubes 14 from the chamber 26. A proprietary gel, Long-Ranger™ from AT Biochemicals, has been found useful for applications using high voltage in the order of 800 V/cm, such as in diagnostic applications. Long-Ranger™ gel allows sequencing rates in the order of 200 bases in 3 minutes with greater than 95% accuracy. 0% C gels provide sequencing rates in the order of 600 bases in two hours at 200 V/cm. Gel temperatures between 20° C. and 35° C. have been found to give good results.

The Long-Ranger gel is prepared within a 50 µm ID capillary by polymerization of a carefully degassed 5% solution of Long-Ranger in a 7M urea, 0.6×TBE buffer. Polymerization is initiated with 0.4 parts per thousand (V/V) TEMED and 0.4 parts per thousand (W/V) ammonium persulphate. Such a gel is stable and may be used for three separations. Use of Long-Ranger gel with a single 50 µm ID capillary has yielded sequencing rates of 3200 bases per hour at 800 v/cm.

The gel may include 0–20% of formamide. Addition of formamide in this range decreases compressions, particularly in the range 10–20%, thereby increasing resolution in regions of compression. However, it has been found that too much (20% or more) formamide reduces the separation rate, theoretical plate count, and resolution for normally migrating fragments without a concomitant decrease in compressions. An optimum concentration of 10% formamide improves resolution of compressed regions without degrading other characteristics of the gel. It has also been found that operating the gel at room temperature is adequate and simplifies the engineering of the analyzer. Results of using formamide have been described in Rocheleau, M. J., et al. Electrophoresis, 13, 484–486, 1992.

The gel should be established in the capillary tubes 14 without voids or bubbles forming during polymerization of the acrylamide due to shrinkage, which may be particularly acute if a bifunctional silane reagent is used to bind the gel to the capillary wall. Such bubbles can be eliminated by use of low percent acrylamide, short columns, adding polyethylene glycol to the monomer mixture (though this is not desired for DNA fragments longer than about 100 bases since it degrades the separation) or by allowing polymerization to occur in a pressured vessel or other methods known in the art.

Also, defects in the gel at the ends 20 may occur when loading samples of DNA into the capillary tubes 14. Such defects are particularly of concern when the capillary tubes 14 are reused. It is therefore desirable to cut off a portion (several millimeters) of the capillary tube 14 after a run. Also, such a defect can be minimized by loading smaller amounts of DNA sample, as much as five times lower, as compared with conventional electrophoresis sequencing of DNA. Thus for example the sample using the apparatus disclosed should be loaded at 150 V/cm for 60 s.

Flaws in the gel can be inspected by visual inspection in a microscope or by passing two laser light beams at an angle through the gel to intersect each other in the gel. Modulated light scatter of the laser light from flaws in the gel may be detected using a collection optic and photomultiplier tube.

Loading of the gel into the capillary tubes 14 also requires care. It is desirable that gel characteristics be uniform from capillary tube to capillary tube. If the capillary tubes are loaded with gel sequentially, differences in the gel may severely degrade the analysis. It is preferable to load the gel monomer into a single container and to fill the capillaries with the gel from the single container simultaneously, as by vacuum syphoning the gel. At high electric fields (in the order of 800 V/cm), the gel can extrude about 50 μm from the detection end of the capillary. To eliminate extrusion, about 2 cm of the gel at the detection end is covalently bonded to the interior walls of the capillary tubes with γ-methacryloxypropyltrimethoxysilance. Such known methods for establishing a gel as described in U.S. Pat. Nos. 4,865,706 and 4,865,707 to Karger et al and 4,810,456 to Bente et al may also be used.

Figure 11A:
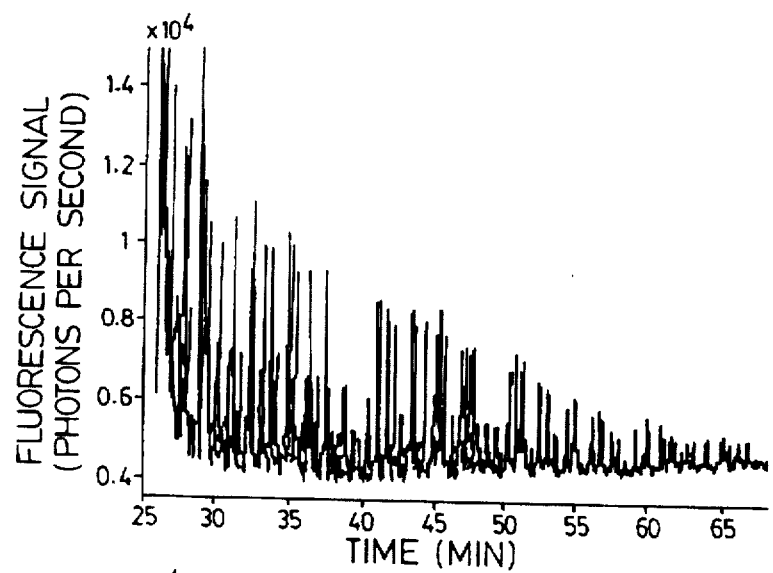
FIGS. 11A, 11B and 11C are graphs showing the results of DNA sequencing using apparatus according to the invention.
Figure 11B:
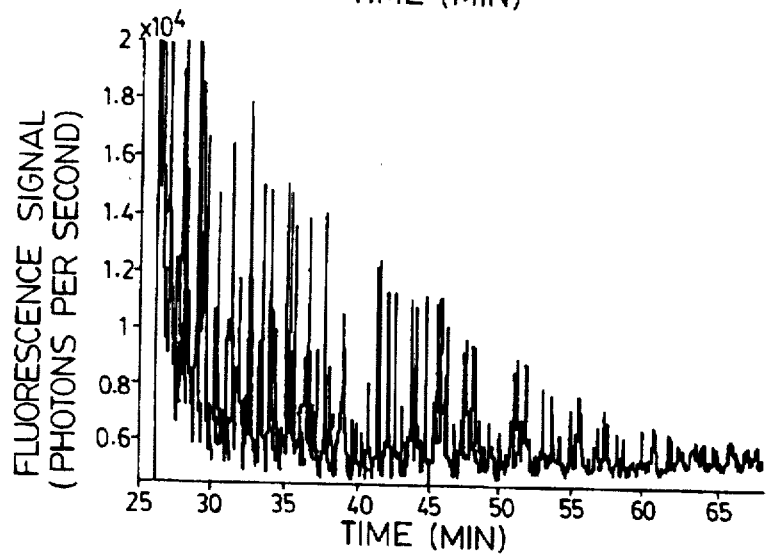
Figure 11C:
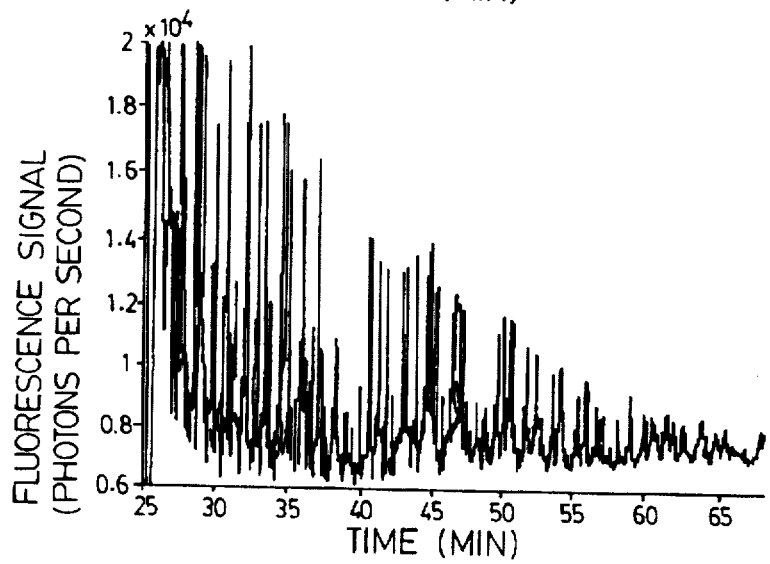

Data has been collected from the system of FIG. 1 with detection at three capillaries using the Tabor and Richardson sequencing technique. An M13mp18 template was used to generate fragments of DNA. Manganese was used instead of magnesium in the sequencing buffer. Sequenase was used for chain extension. A FAM labeled primer is used and a single sequencing reaction is performed with ddATP, ddCTP, ddGTP and ddTTP present in a 8:4:2:1 ratio. A 50 μm capillary was filled with 4% T, 5% C gel and operated at 200 V/cm. For a run of 330 bases in 70 minutes, comparable data was obtained as for single capillary systems, although the throughput was 850 bases/hour for a 3 capillary system. FIGS. 11a, 11b and 11c show the results of the sequencing.

Resolution is limited to fragments less than 300 bases in length at high voltages near 800 V/cm. Generally speaking, retention time increases linearly with fragment length for a given high V/cm until the mobility of the fragments approaches a limiting value and no separation is achieved. This is called biased reptation. As the electric field increases, the transition to biased reptation moves to shorter fragments. Biased reptation is highly undesirable since it causes sequencing fragments to coelute, destroying the separation resolution. Hence for longer fragments (in the order of 600 bases), the electric field can be decreased to about 140 V/cm, with an increase in separation time. Moderate gel temperature (in the order of 20° to 35° C.) can assist in improving sequencing rate, though it does not appear to strongly affect the transition from reptation to biased reptation. Lower % T acrylamide gels can also assist in the sequencing of longer fragments.

The analyzer described here has utility for a wide variety of applications, with some modifications. In each case there is some means to force analyte through the capillaries, the capillaries are held in the chamber as shown in FIGS. 1 and 2 for example, and sheath fluid is supplied through the cuvette, with the sheath fluid preferably having the same index of refraction as the fluid carrying the analyte.

Figure 12:
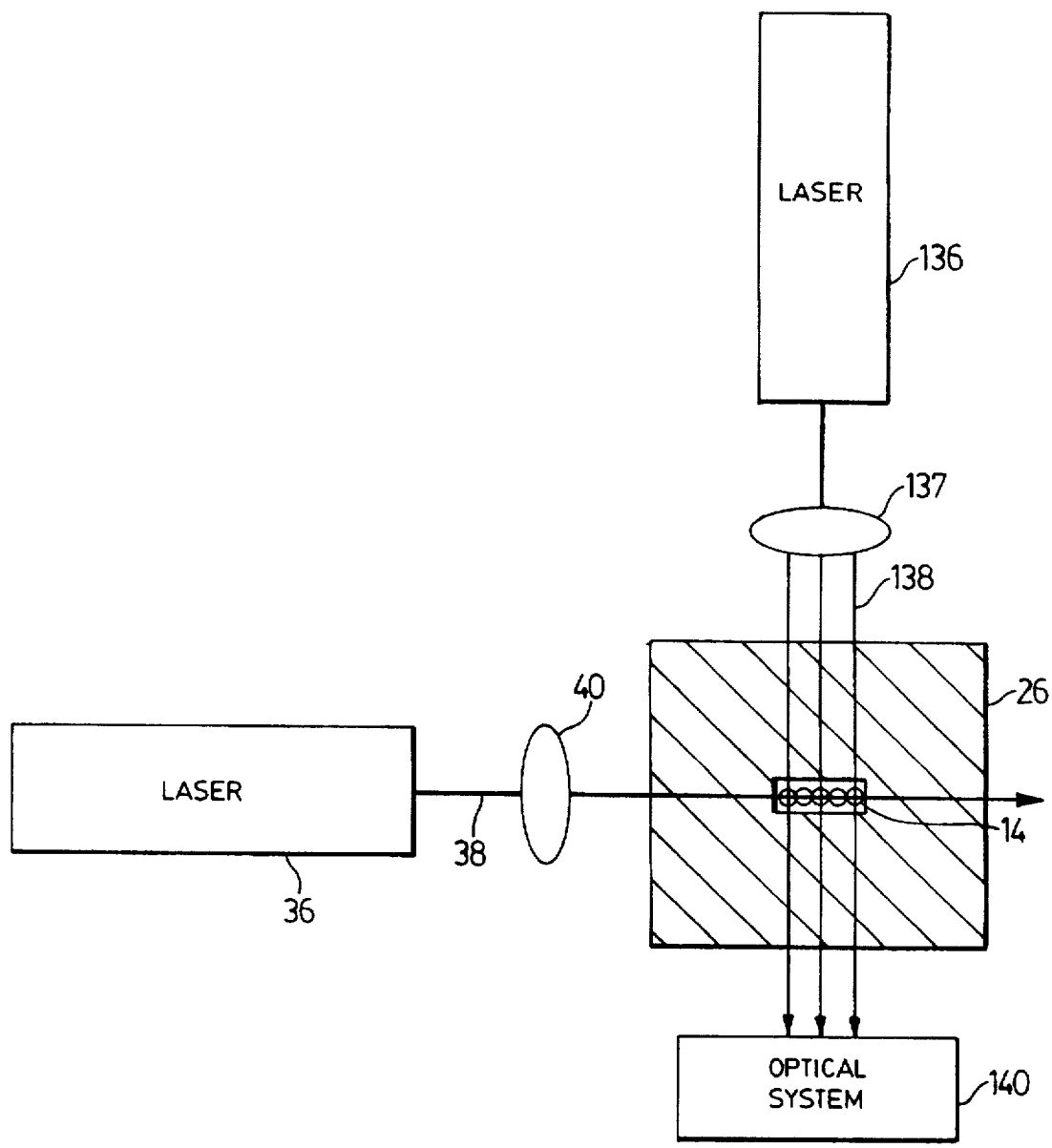
FIG. 12 shows a schematic of a further method of detecting analyte.

The detection of analyte may also be accomplished using thermooptical absorption. In this technique, the laser 36 is used to excite the analyte which tends to heat the analyte and change the index of refraction of the fluid by which it is carried. As shown in FIG. 12, the deflection of the beams 138 from a second laser 136 after collimating with an appropriate optic 137 by the sample fluid emerging from the ends of the capillary tubes 14 is then detected by the optical system 140, which may be designed as shown in FIG. 1.

Figure 13:
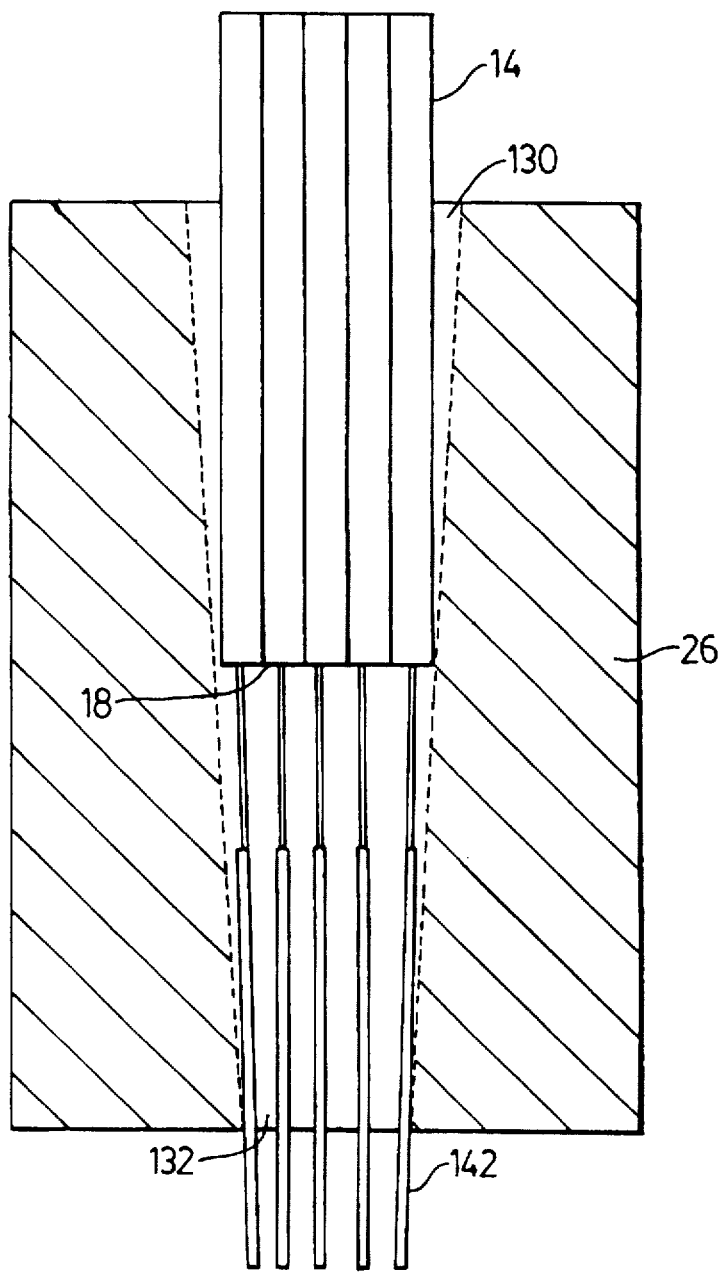
FIG. 13 shows an apparatus for use for the electrochemical detection of analyte.

An analyzer for use as an electrochemical detector is shown in FIG. 13. Electrodes 142 enter the chamber 26 (made of an inert non-conducting material such as quartz) from the bottom end 132 of the chamber. Each electrode 142 is connected to an amplifier (not shown), and the output of the amplifier is provided to a processor, for example a computer, through an interface for analysis in accordance with known principles (similar to the optical processing of the signals). In such a case, the laser 36 is not required, since the identification of the sample is by electrochemical analysis. Multiple capillaries allow for rapid analysis.

The analyzer may also be used to detect impurities in fluids by detecting light scatter. In such a case, the high voltage source 30 is not required, since the fluid may be pumped directly as a fluid through the capillary tubes, nor is the spectral filter 60 required since the total intensity of the scattered light may be detected. The GRIN lenses 44 and detectors 52 detect variations in the scatter of light resulting from particles or impurities in the fluid.

The analyzer is also useful for the detection of organic contaminants, for example the fluorescent detection of polycyclic aromatic hydrocarbons. In such detection, the capillary tubes are filled with chromatographic packing material (coated silica beads) instead of a polymer and the analyte sample is forced through the capillary tubes using a pump instead of the high voltage source 30. The laser 36 should emit radiation at about 330 nm or such other appropriate wavelength for detection of organic contaminants. Fluorescence emitted by the sample of contaminant is detected through an appropriate spectral filter 60 and the optical apparatus shown for example in FIG. 1.

In a further example, the analyzer may be used for flow cytometry. In flow cytometry a sample containing cells taken from an animal or human body by fine needle aspiration is stained using a fluorescent reagent such as a nucleic acid stain or antibodies. With the present analyzer, the sample is forced under air pressure by a pump that replaces the high voltage source 30 through the capillary tubes 26 and the laser beam 38 is passed through the sample as it emerges from the capillary tubes 26 into the sheath flow. The intensity of the fluorescence from the fluorescent reagent is detected using the optical system of FIG. 1 and used to estimate the number of sets of chromosomes in the cells, and this is useful, in accordance with known procedures in the diagnosis and prognosis of cancer.

Multiple capillary tubes may also be used to spray analyte into a mass spectrometer. In such a case, the capillaries are bundled within a circular or polyhedral cuvette with sheath flow about the capillaries. The bundle of capillaries is inserted into the ionization chamber of a mass spectrometer such as the triple quadrupole mass spectrometer sold by Sciex Division of MDS Health Group Limited, of Thornhill, Ontario, Canada, under its trademark TAGA 6000E. For electrospray of analyte, the capillary tubes are made conducting at the end that extends into the ionization chamber. Electrical potential is applied to the ends of the capillaries in known manner.

Figure 14:
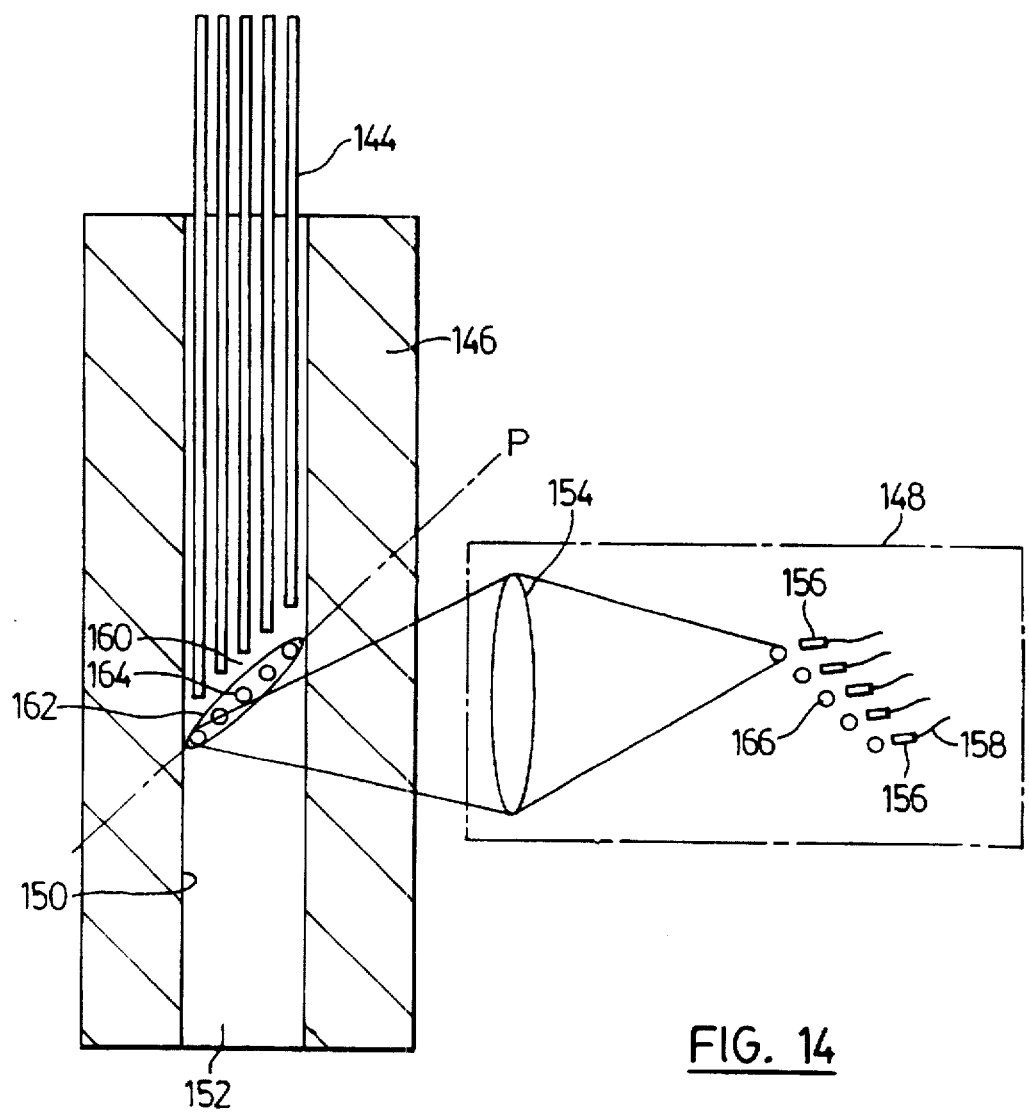
FIG. 14 is a schematic section of an analyzer having a rectangular (in this case square) array in a square flow chamber.
Figure 15:
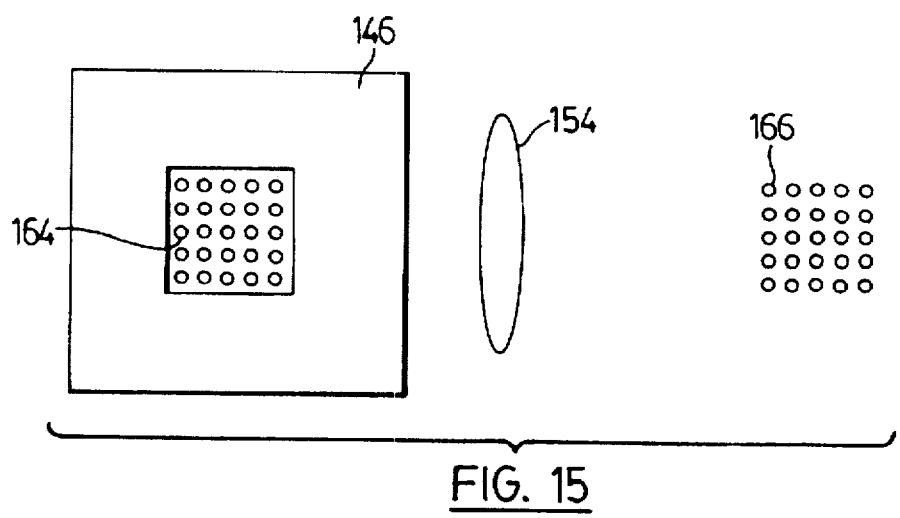
FIG. 15 is a schematic view from the bottom of the chamber of FIG. 14.
Figure 16:
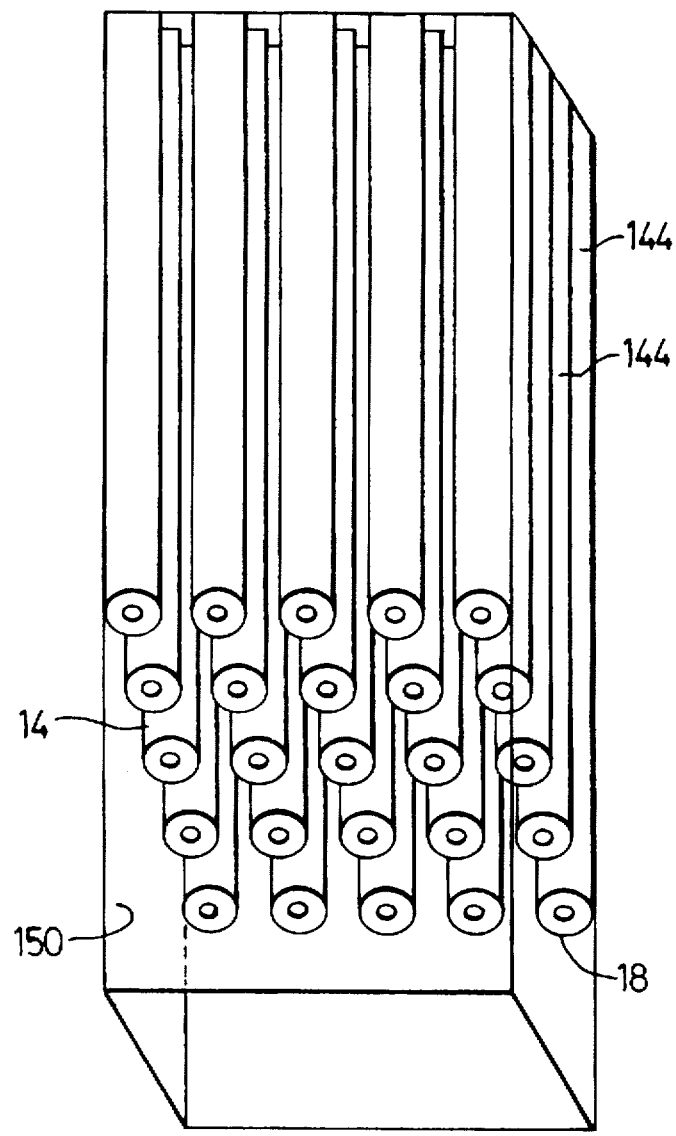
FIG. 16 is an isometric view of a square grid of capillaries for insertion in the chamber of FIG. 14.

A square, rectangular or other suitable polyhedral array of capillary tubes may also be used as well, as shown in FIGS. 14, 15 and 16 for the case of a square capillary array. The array may be rectangular as well. Other polyhedral arrays could be used in principal, but this complicates the optics. The array of capillary tubes 14 is formed from five rows 144 of five capillary tubes 14 each, all bound within a square chamber 146 forming part of a square sheath flow cuvette. The cuvette is similar to the cuvette shown in FIGS. 4–9 only the central chamber is square. An optical system 148 disposed adjacent the cuvette includes a collection optic 154, GRIN lenses 156, and optic fibres 158 leading to photodiodes and the balance of the optical system as shown in FIG. 1.

Each row 144 of capillary tubes is similar to the row shown in FIG. 1, but succeeding rows in the direction of the optical system 148 terminate higher in the sheath flow cuvette as shown at 160. All capillary tubes 14 in a row terminate adjacent each other. Sheath flow is provided about all of the tubes 14 within the sheath flow cuvette. All four walls 150 of the sheath flow cuvette taper inward towards the bottom 152 of the chamber. The ends of the capillary tubes 14 define a sloping plane P, sloping downward and away from the optical system 148. An elliptical or other linear cross-section laser beam 162 oriented at the same slope as the sloping plane (or close to it) is directed just below the ends of the capillary tubes 14. Fluorescence of the samples forms a sloping square array of fluorescent spots 164 that appears as a square grid of spots 166 from a view at right angles to the cuvette.

Fluorescence from sample streams emerging from the capillary tubes 14 is collected by an optic 154 and imaged on to the square array of GRIN lenses 156, which lie in the image plane of the fluorescent spots produced by the optic 154. The GRIN lenses 156 are oriented with their faces perpendicular to the wavefront from the collection optic 154. Light collected by the GRIN lenses is transmitted through optic fibres to photodetectors of the type shown in FIG. 1.

It is possible to operate the cuvette upside down to allow bubbles in the sheath stream to move upward with the stream to waste.

A person skilled in the art could make immaterial modifications to the invention described and claimed in this patent document without departing from the essence of the invention.

The embodiments of the invention in which an exclusive property or privilege is claimed as defined as follows:

1. An analyzer for analyzing an organic sample, the analyzer comprising:

a plurality of capillary tubes arrayed side by side, each capillary tube having first and second ends, the second ends of the capillary tubes terminating adjacent each other and the first ends being connectable to a source of organic sample;

a flow chamber having an interior cavity, the second ends of the capillary tubes terminating inside the interior cavity;

means to supply sheath fluid into the interior cavity of said flow chamber to provide a flow of sheath fluid past the second ends of the capillary tubes such that any organic sample in said capillary tubes is drawn by the flow of sheath fluid in individual sample streams from the second ends of the capillary tubes;

means to force said organic sample through the capillary tubes from the first ends of the capillary tubes to the second ends of the capillary tubes;

a detector positioned to detect organic sample in the individual sample streams emerging from the capillary tubes; and a non-capillary sized waste outlet, independent of said means to force organic sample, positioned in said flow chamber for draining said sheath flow fluid and entrained sample streams directly from said flow chamber to waste, said waste outlet draining the entrained sample streams and associated sheath flow fluid from a plurality of said capillary tubes.

2. The analyzer according to claim 1, wherein the detector includes a source of collimated electromagnetic radiation having a wavelength for exciting the sample to emit radiation, said source being aligned to provide collimated light through the organic sample drawn from the capillary tubes by the sheath fluid.

3. The analyzer according to claim 2, wherein the detector further includes an optical system aligned to receive emitted radiation from the organic sample.

4. The analyzer according to claim 3, in which the optical detection system further comprises a wave length division demultiplexer for separating emitted radiation into light of at least two spectral bands, and at least two photodetectors for each capillary tube, one for each of said spectral bands.

5. The analyzer according to claim 2, in which said capillary tubes are arrayed in a linear array.

6. The analyzer according to claim 2, wherein the detector comprises an optical system for receiving scattered radiation from contaminants carried by said sample.

7. The analyzer according to claim 2, wherein said flow chamber includes an upper portion and a lower portion, and said means to supply sheath fluid comprises a tube connected to the upper portion of the flow chamber and wherein the lower portion of said flow chamber encircles the second ends of the capillary tubes.

8. The analyzer according to claim 7, wherein at least a portion of the lower portion of the chamber is made of transparent material, said portion being adjacent the second ends of the capillary tubes.

9. The analyzer according to claim 2, wherein a fluid acceleration region is formed downstream of the second ends of said capillaries, and wherein said source of collimated electromagnetic radiation is positioned to direct said radiation at the fluid acceleration region.

10. The apparatus according to claim 2, wherein said detector further comprises an optical collection means positioned to collect radiation emitted by said sample in a direction generally orthogonal to the direction of flow of said sample streams.

11. The analyzer according to claim 1, wherein the means to force the organic sample through the capillary tubes includes an electrophoretic voltage source connected across the length of the capillary tubes.

12. The analyzer according to claim 1, wherein said capillary tubes are arrayed in a linear array.

13. The analyzer according to claim 1, wherein the means to supply sheath flow into said interior cavity includes a reservoir of sheath fluid, syphon coupled to the flow chamber.

14. The apparatus according to claim 13, wherein said detector further comprises a source of collimated electromagnetic radiation for generating electromagnetic radiation in a first direction which is generally orthogonal with respect to the direction of flow of said sample streams and an optical collection means positioned to receive radiation emitted from said sample streams in a second direction which is generally orthogonal with respect to the direction of flow of said sample streams.

15. The analyzer according to claim 1, wherein said flow chamber comprises a side wall at least partially encircling said interior cavity and wherein at least a segment of the side wall being transparent to electromagnetic radiation radiating away from organic sample drawn from the capillary tubes by the sheath fluid.

16. The analyzer according to claim 1, wherein said chamber comprises a side wall at least partially encircling said interior cavity and wherein at least a segment of the side wall being transparent to electromagnetic radiation radiating away from organic sample drawn from the capillary tubes by the sheath fluid and at least a further segment of the side wall being transparent to the collimated electromagnetic radiation.

17. The apparatus according to claim 16, wherein said detector further comprises a source of collimated electromagnetic radiation for generating electromagnetic radiation in a first direction which is generally orthogonal with respect to the direction of flow of said sample streams and an optical collection means positioned to receive radiation emitted from said sample streams in a second direction which is generally orthogonal with respect to the direction of flow of said sample streams.

18. The analyzer according to claim 1, wherein each of said capillary tubes has an inside diameter of about 50 μm and an outside diameter on the order of about 150 μm.

19. The analyzer according no claim 1, wherein said means to force an organic sample through the capillary tube comprises an electrophoretic voltage source of about 30 kv connected across said capillary tubes and said flow chamber.

20. The analyzer according to claim 19, further comprising means for distributing forces between capillaries generated by said voltage source.

21. The analyzer according to claim 1, wherein the organic material is carried in said capillaries by a fluid, said fluid having essentially the same index of refraction as the sheath fluid.

22. The analyzer according to claim 1, wherein the volumetric flow of sheath fluid through said chamber is less than about 10 mL/hr.

23. The analyzer according to claim 1, wherein the rate flow of sheath fluid through said chamber is less than about 4 mm/sec.

24. The apparatus according to claim 1, wherein said detector further comprises a source of collimated electromagnetic radiation for generating electromagnetic radiation in a first direction which is generally orthogonal with respect to the direction of flow of said sample streams and an optical collection means positioned to receive radiation emitted from said sample streams in a second direction which is generally orthogonal with respect to the direction of flow of said sample streams.

\* \* \* \* \*